United States Patent
Porter et al.

(10) Patent No.: US 10,166,125 B2
(45) Date of Patent: *Jan. 1, 2019

(54) TRANSDERMAL INTRAOSSEOUS DEVICE

(71) Applicant: Biomet Manufacturing, LLC, Warsaw, IN (US)

(72) Inventors: Joshua R. Porter, Winona Lake, IN (US); Troy W. Hershberger, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 114 days.

This patent is subject to a terminal disclaimer.

(21) Appl. No.: 14/974,636

(22) Filed: Dec. 18, 2015

(65) Prior Publication Data

US 2016/0100961 A1    Apr. 14, 2016

Related U.S. Application Data

(60) Continuation of application No. 13/969,693, filed on Aug. 19, 2013, now Pat. No. 9,254,194, which is a
(Continued)

(51) Int. Cl.
| | | |
|---|---|---|
| *A61F 2/78* | (2006.01) | |
| *B24C 1/04* | (2006.01) | |
| *A61F 2/28* | (2006.01) | |

(52) U.S. Cl.
CPC ............. *A61F 2/78* (2013.01); *A61F 2/28* (2013.01); *B24C 1/04* (2013.01);
(Continued)

(58) Field of Classification Search
CPC ...... A61F 2/78; A61F 2/2814; A61F 2/30749; A61F 2002/7887
See application file for complete search history.

(56) References Cited

U.S. PATENT DOCUMENTS

| 3,947,897 A | 4/1976 | Owens |
|---|---|---|
| 4,158,895 A | 6/1979 | Frosch et al. |
| (Continued) | | |

FOREIGN PATENT DOCUMENTS

| GB | 2139095 A | 7/1984 |
|---|---|---|
| JP | 61200903 A | 9/1986 |
| (Continued) | | |

OTHER PUBLICATIONS

"Regenerex Porous Titanium Construct", brochure, Biomet Orthopedics, Inc. 2008, 7 sheets.*
(Continued)

*Primary Examiner* — Marcia Watkins
(74) *Attorney, Agent, or Firm* — Schwegman Lundberg & Woessner, P.A.

(57) ABSTRACT

A transdermal intraosseous device includes a transdermal adapter for an external prosthetic device for a bone of a patient and a bone fixator including a distal portion coupled to the transdermal adapter and a proximal portion for anchoring into the bone. The transdermal adapter includes a dome-shaped portion for transcutaneous implantation and an external shaft extending from the dome-shaped portion. A dermal transition structure is configured to include a controlled roughness gradient from the external shaft to the dome-shaped portion and configured for use in infection control at a dermis layer of the patient.

13 Claims, 10 Drawing Sheets

Related U.S. Application Data division of application No. 13/016,766, filed on Jan. 28, 2011, now Pat. No. 8,512,416.

(60) Provisional application No. 61/300,277, filed on Feb. 1, 2010.

(52) U.S. Cl.
CPC ............... *A61F 2002/7887* (2013.01); *A61F 2220/0008* (2013.01); *A61F 2250/0023* (2013.01); *A61F 2250/0025* (2013.01)

(56) References Cited

U.S. PATENT DOCUMENTS

| | | | |
|---|---|---|---|
| 4,781,720 A | | 11/1988 | Sherva-parker |
| 5,057,101 A | * | 10/1991 | Dorr ............... A61F 2/30724 623/23.23 |
| 5,478,237 A | | 12/1995 | Ishizawa |
| 5,489,306 A | | 2/1996 | Gorski |
| 6,197,065 B1 | | 3/2001 | Martin et al. |
| 6,482,238 B1 | | 11/2002 | Grundei |
| 6,485,522 B1 | | 11/2002 | Grundei |
| 6,508,841 B2 | | 1/2003 | Martin et al. |
| 6,712,855 B2 | | 3/2004 | Martin et al. |
| 6,869,450 B2 | | 3/2005 | Grundei |
| 7,014,661 B2 | | 3/2006 | Blunn et al. |
| 7,141,073 B2 | | 11/2006 | May et al. |
| 7,323,013 B2 | | 1/2008 | McTighe et al. |
| 7,374,577 B2 | | 5/2008 | Kim et al. |
| 7,476,254 B2 | | 1/2009 | White et al. |
| 7,578,851 B2 | | 8/2009 | Dong et al. |
| 7,722,678 B2 | | 5/2010 | Brown et al. |
| 8,512,416 B2 | | 8/2013 | Porter et al. |
| 9,254,194 B2 | | 2/2016 | Porter et al. |
| 2001/0039454 A1 | | 11/2001 | Ricci et al. |
| 2002/0099449 A1 | * | 7/2002 | Speitling ............ A61F 2/30767 623/23.72 |
| 2003/0109878 A1 | | 6/2003 | Grundei |
| 2003/0171825 A1 | * | 9/2003 | Blunn ................. A61C 8/0018 623/32 |
| 2003/0195636 A1 | | 10/2003 | Coop |
| 2004/0006396 A1 | | 1/2004 | Ricci et al. |
| 2004/0068324 A1 | * | 4/2004 | Grundei ............... A61F 2/2814 623/32 |
| 2004/0191727 A1 | | 9/2004 | Shelemay et al. |
| 2005/0102038 A1 | * | 5/2005 | Grundei ............... A61F 2/2814 623/23.46 |
| 2005/0119758 A1 | | 6/2005 | Alexander et al. |
| 2006/0041318 A1 | | 2/2006 | Shannon |
| 2006/0105015 A1 | * | 5/2006 | Perla ..................... A61L 27/32 424/423 |
| 2007/0073412 A1 | | 3/2007 | Blunn et al. |
| 2007/0150068 A1 | | 6/2007 | Dong et al. |
| 2008/0147187 A1 | | 6/2008 | Bollinger et al. |
| 2009/0149966 A1 | | 6/2009 | Blunn et al. |
| 2009/0292368 A1 | | 11/2009 | Plowman et al. |
| 2013/0337724 A1 | | 12/2013 | Porter et al. |

FOREIGN PATENT DOCUMENTS

| | | | | |
|---|---|---|---|---|
| JP | 04183463 A | | 6/1992 | |
| JP | 2523686 B2 | * | 8/1996 | ............... A61F 2/78 |
| WO | WO 2009105535 A1 | * | 8/2009 | ........... A61F 2/2814 |

OTHER PUBLICATIONS

"U.S. Appl. No. 13/969,693, Non Final Office Action dated Jan. 30, 2015", 7 pgs.

"U.S. Appl. No. 13/969,693, Notice of Allowance dated Oct. 2, 2015", 5 pgs.

"U.S. Appl. No. 13/969,693, Response filed May 29, 2015 to Non Final Office Action dated Jan. 30, 2015", 6 pgs.

"Compress® Compliant Pre-Stress", Brochure, Biomet Orthopedics, Inc.,, (2009), 42 pgs.

"ENDO-EXO: New! Endo-Exo Prosthesis", ESKA Australia, Specialists in Orthopaedic Implants, Product Review, [Online]. Retrieved from the Internet: <http://www.eskaaustralia.com.au/products_endo.html>,accessed Aug. 1, 2011, 2 pgs.

"Limb Salvage Product Portfolio", brochure, Biomet Orthopedics, Inc, (2009), 23 pgs.

"The Osseotite® Implant, The Surface That Succeeds. Proven Performance and Predictable", brochure, Biomet 31 LLC, Inc., (2009), 8 pgs.

"The Osseotite® Implant-Documented Sucess", brochure, Biomet 3i LLC, Inc, (Apr. 2012), 8 pgs.

Branemark, Rickard, et al., "Osseointegration in skeletal Reconstruction and Rehabilitation", Journal of Rehabilitation Research & Development, vol. 38 No. 2, [Online]. Retrieved from the Internet: <http://www.rehab.research.va.gov/jour/01/38/2/brane382.htm>,accessed Jul. 29, 2011, (Mar./Apr. 2001), 8pgs.

Fitzpatrick, Noel, "Intraosseous Transcutaneous Amputation Prosthesis, An Alternative to Limb Amputation in Dogs and Cats", Society of Practising Veterinary Surgeons, SPVS Review, (2009), 2-5.

Isackson, Dorthyann, et al., "Dermal Barriers to Prevent Infection of Percutaneous Implants", abstract, Society for Biomaterials, Translational Research Symposium, Atlanta, Georgia,, (Sep. 11-13, 2008), 3 pgs.

Mitutoyo, "Surface Roughness Measurement: Practical Tips for Laboratory and Workshop:", Mitutoyo America Coporation, Auroa IL,, (2009), 8 pgs.

Pendegrass, C. J., et al., "Sealing the skin barrier around transcutaneous implants", The Journal of Bone and Joint Surgery, vol. 90-B, No. 1, (Jan. 2008), 114-121.

Pitkin, Mark, "Skin and bone integrated prosthetic pylon: A pilot animal study", Journal of Rehabilitation Reseasrch & Development, vol. 43, No. 4,. (Jul./Aug. 2006), 7 pgs.

\* cited by examiner

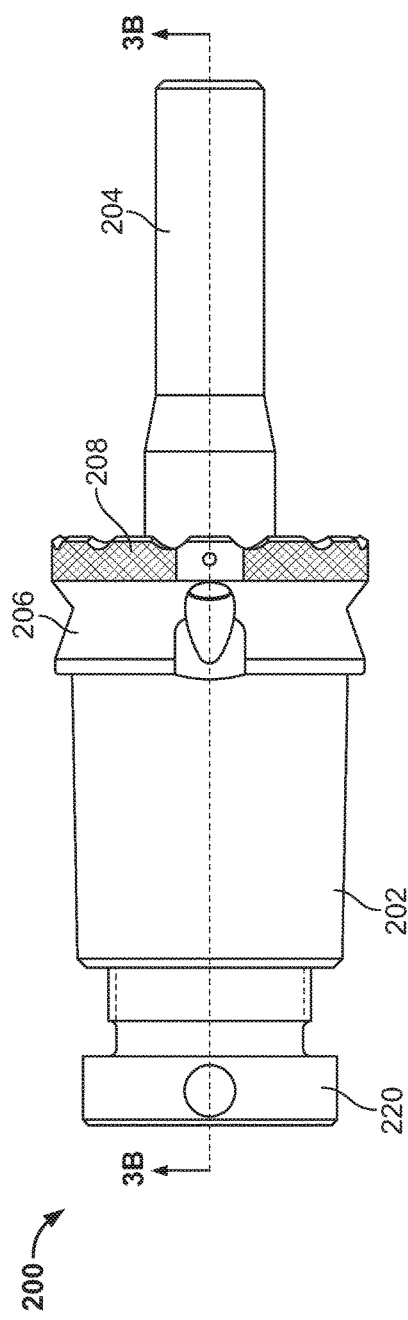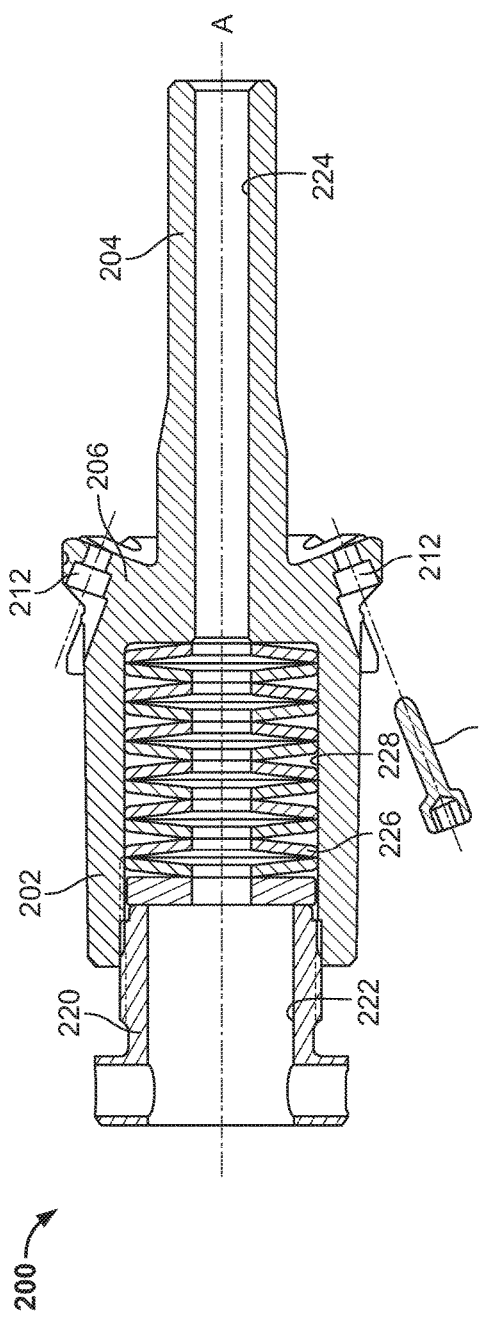
FIG. 3A
FIG. 3B

TRANSDERMAL INTRAOSSEOUS DEVICE

CROSS-REFERENCE TO RELATED APPLICATIONS

This application is a continuation of U.S. patent application Ser. No. 13/969,693 filed on Aug. 19, 2013, now issued as U.S. Pat. No. 9,254,194 on Feb. 9, 2016, which is a divisional of U.S. patent application Ser. No. 13/016,766 filed on Jan. 28, 2011, now issued as U.S. Pat. No. 8,512,416 on Aug. 20, 2013, which claims the benefit of U.S. Provisional Patent Application No. 61/300,277 filed on Feb. 1, 2010. The disclosures of the above applications are incorporated herein by reference.

INTRODUCTION

Various known external fixation devices for amputation or trauma include compliant mechanisms for supporting a prosthetic device to a bone. In devices of this type, the compliant fixation mechanism provides a compressive stress at the bone interface for preventing bone resorption over time. Typically, a metal portion of the fixation device may extend beyond the cut surface of the bone, such that soft tissue is attached to the metal, rather than the bone.

The interface between the prosthetic device and soft tissue can be a source of infection. The present teachings provide devices and surface treatments associated with the transcutaneous portion of an external prosthesis adapter.

SUMMARY

The present teachings provide a transdermal intraosseous device that includes a transdermal adapter for an external prosthetic device for a bone of a patient and a bone fixator including a distal portion coupled to the transdermal adapter and a proximal portion for anchoring into the bone. The transdermal adapter includes a dome-shaped portion for transcutaneous implantation and an external shaft extending from the dome-shaped portion. A dermal transition structure is configured to include a controlled roughness gradient from the external shaft to the dome-shaped portion and configured for use in infection control at a dermis layer of the patient. The bone fixator can be a compliant bone fixator or a static, non-compliant bone fixator.

In some embodiments, the dermal transition structure includes a porous metal dome-shaped structure surrounding and overlaying the dome-shaped portion of the transdermal adapter, and first and second transitional surface treatment layers between the external shaft and the porous metal dome-shaped structure along the longitudinal axis of the transdermal adapter. The first transitional surface treatment layer is roughened by blasting for contact with the dermis and the second transitional surface treatment layer is roughened by a combination of blasting treatment and acid-etching treatment for contact with the dermis.

The present teachings also disclose a method for providing a controlled roughness gradient transition between an external prosthetic device for a bone of a patient and the corresponding dermis of the patient. The method includes positioning a porous metal dome-shaped structure around a metal dome-shaped portion of a transdermal adapter. An external shaft extends from the dome-shaped portion of the transdermal adapter and a first portion of the external shaft is roughened by blasting. A second portion of the external shaft is roughened by blasting and acid etching. The first portion extends above the porous metal dome-shaped structure along a longitudinal axis of the external shaft and the second portion extends above the first portion along the longitudinal axis of the external shaft. The porous meal dome-shaped portion and the first and second portions of the external shaft are configured to contact the dermis for infection control.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 3A is a plan view of a compliant fixator of the transdermal intraosseous device of FIG. 2;

FIG. 3B is a sectional view of the compliant fixator of FIG. 3A taken along the line 3B-3B;

DESCRIPTION OF VARIOUS EMBODIMENTS

Figure 1:
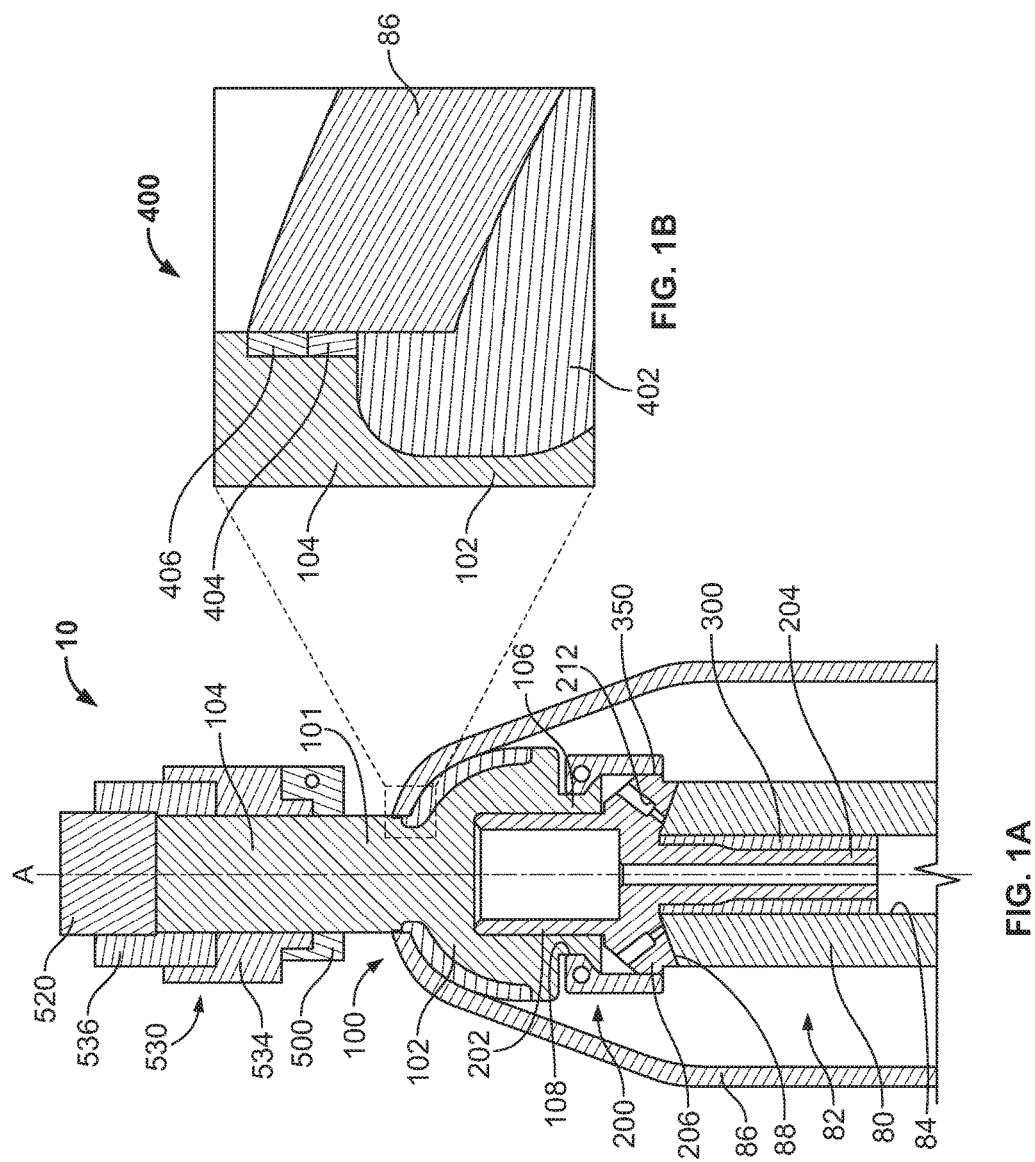
FIG. 1A is an environmental cross-sectional view of an exemplary transdermal intraosseous device according to the present teachings.
FIG. 1B is an enlarged detail of FIG. 1A.

The following description is merely exemplary in nature and is in no way intended to limit the present teachings, applications, or uses. The present teachings can be used for attaching any external prosthetic device to a bone through skin via a transdermal intraosseous device. The transdermal intraosseous device can include a transdermal adapter and an intraosseous fixator. In some embodiments, the intraosseous fixator can optionally include a compliant fixator, such as, for example, the Compress® Pre-Stress Implant, which is commercially available from Biomet, Inc. Warsaw, Ind., or a compliant fixator according to the present teachings and described herein. Compliance, as used herein, is a measurement of softness as opposed to stiffness of a material. Compliance of a structural member is generally the reciprocal of Young's modulus (one dimension) or the inverse of the stiffness matrix (more than one dimensions). Accordingly, a compliant member is generally a structural member that has enhanced compliance, such as an elastic spring, bellows, Belleville washers and other elastically biasing members. The compliant fixator of the present teachings, as well as the Compress® Compliant Pre-Stress Implant, allows osseointegration at the bone/implant interface and can provide a stable, high-pressure/implant interface. The compliant fixator can also assist in the prevention of stress shielding and any concomitant bone loss.

Infection is generally a common complication with known transdermal (transcutaneous) intraosseous devices. Aggressive apical epithelial migration, or epithelial downgrowth may be initiated as a normal wound healing process to foreign bodies. If not prevented, this process may result in deep pocket formation and subsequent marsupialization of the transdermal devices. In contrast, subepithelial connective tissue adhesion to a transdermal intraosseous device may prevent epithelial downgrowth and associated complications, such as infection.

As discussed below, the transdermal intraosseous device of the present teachings can include a transdermal adapter coupled to an intraosseous fixator, such as a compliant fixator or other intramedullary anchoring member. The transdermal adapter can include a porous titanium material, such as Regenerex® Porous Titanium Construct, commercially available from Biomet, Inc., Warsaw, Ind. Similarly to Regenerex®, the porous titanium material may have an average porosity of about 67 percent and pore size ranging from about 100 to about 600 microns (average of 300 microns), as well as high strength and flexibility Referring to FIGS. 1A-7B, an exemplary transdermal intraosseous device 10 according to the present teachings can include a transdermal adapter 100 for connection to an external prosthetic device (not shown) and a bone fixator 200 for compliant or non-compliant fixation into an intramedullary bore 84 of a bone 80, such as a femur, tibia, humerus, etc., that will receive the external prosthetic device. Accordingly, the bone fixator 200 can be a compliant fixator that can provide pre-stress to the bone or a non-compliant fixator in the form of a static (non-dynamic) anchoring member.

The bone fixator 200 can include a distal portion 202 and a proximal portion 204. The distal portion 202 is configured for coupling with the transdermal adapter 100 outside the bone 80 in the subdermal soft tissue 82 under the epidermis and dermis layers (skin) 86 of the patient, such as, for example, with a taper connection, as discussed below. The proximal portion 204 is received into the bore 84 of the bone 80 for anchoring into the bone 80 as discussed below. The bone fixator 200 can also include an intermediate portion 206 between the distal portion 202 and the proximal portion 204 of the bone fixator 200. The intermediate portion 206 can be a skirt-like collar and can be modularly or fixedly coupled to the distal portion 202 and the proximal portion 204 and can include a porous titanium plasma spray 208 (FIG. 3A) with a hydroxyapatite (HAS) coating or other similar treatment for increased biologic fixation. The intermediate portion 206 can be fixed to a resected distal surface 88 of the bone 80 with anti-rotation pins or other fasteners 210 through corresponding apertures 212 at an angle relative to a longitudinal axis A of the bone fixator 200, as shown in FIG. 3B. As shown in FIG. 1A, the longitudinal axis A is also a center axis of the transdermal adapter 100.

Figure 8:
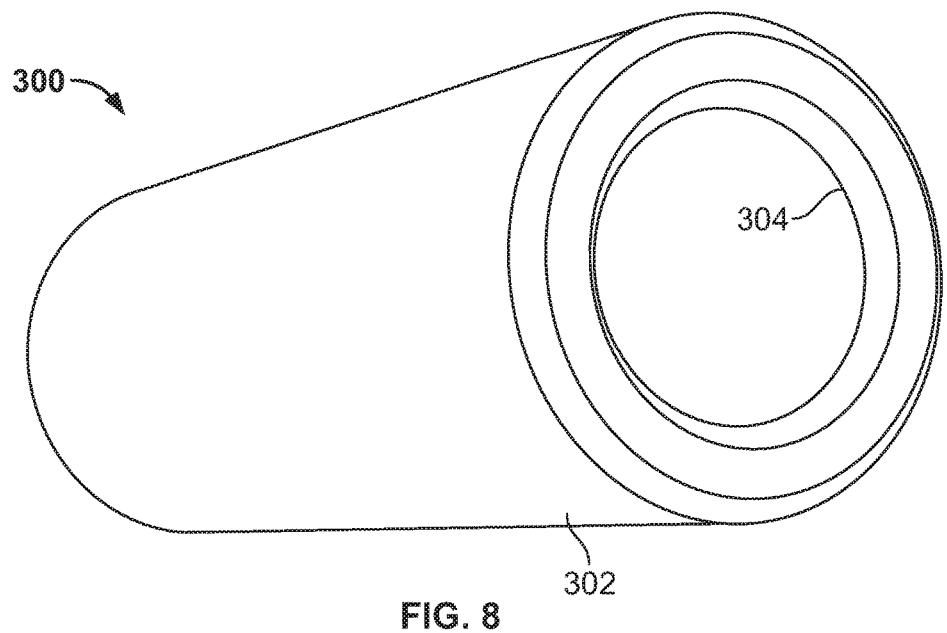
FIG. 8 is a perspective view of a patient-specific sleeve of an exemplary transdermal intraosseous device according to the present teachings.

Referring to FIGS. 1A and 8, the transdermal intraosseous device 10 can include a centering sleeve 300. The centering sleeve 300 can include an outer surface 302 engageable with the bone bore 84 and an inner surface 304 receiving and engaging the proximal portion 204 of the bone fixator 200. In some embodiments, the centering sleeve 300 can be patient-specific (customized for an individual patient). For example, the outer surface 302 of the centering sleeve 300 can be patient-specific (customized for an individual patient) to conform to the surface of the bone bore 84 based on a three-dimensional image of the bone bore 84. The a three-dimensional image of the bone bore 84 can be generated via MRI, CT or other imaging methods of the patient's anatomy during a pre-operative planning phase of the surgical procedure using computer modeling technology commercially available, for example, by Materialise USA, Plymouth, Mich. Accordingly, the outer surface 302 of the centering sleeve 300 can include, for example, patient-specific, cylindrical or piece-wise cylindrical, conical or other curved and closed surface portions. The inner surface 304 of the centering sleeve 300 can be configured to receive and engage the proximal portion 204 of standard (non-custom) bone fixators 200 of different standard sizes and can be, for example, tapered, cylindrical, piece-wise cylindrical or piece-wise tapered. In this regard, the centering sleeve 300 provides a transition from a patient-specific engagement with the bone 80 of the patient to a standard engagement with one of the standard size bone fixators 200.

Figure 6A:
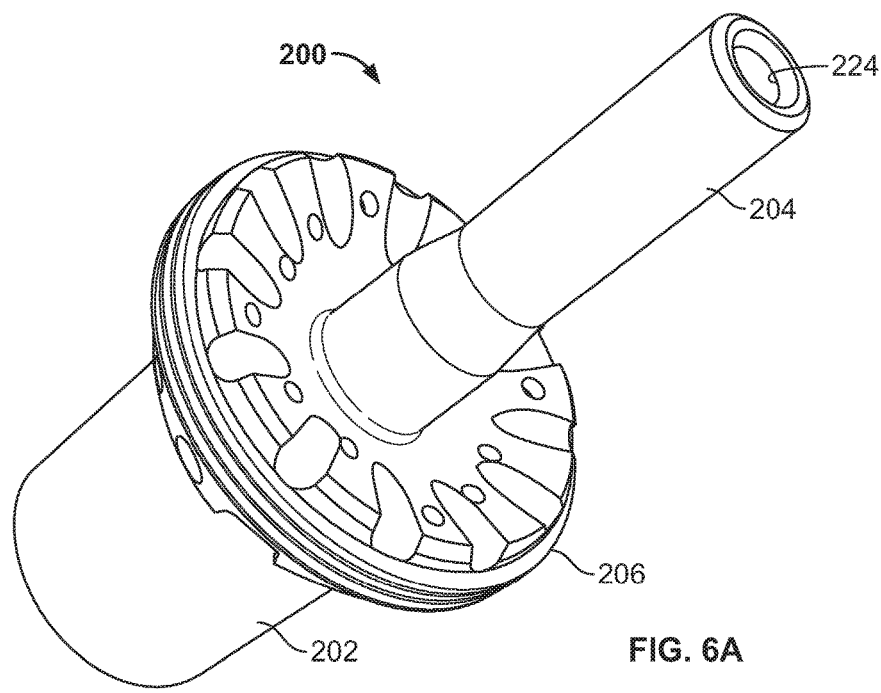
FIGS. 6A-6C are various perspective views of a compliant fixator for an exemplary transdermal intraosseous device according to the present teachings.
Figure 6B:
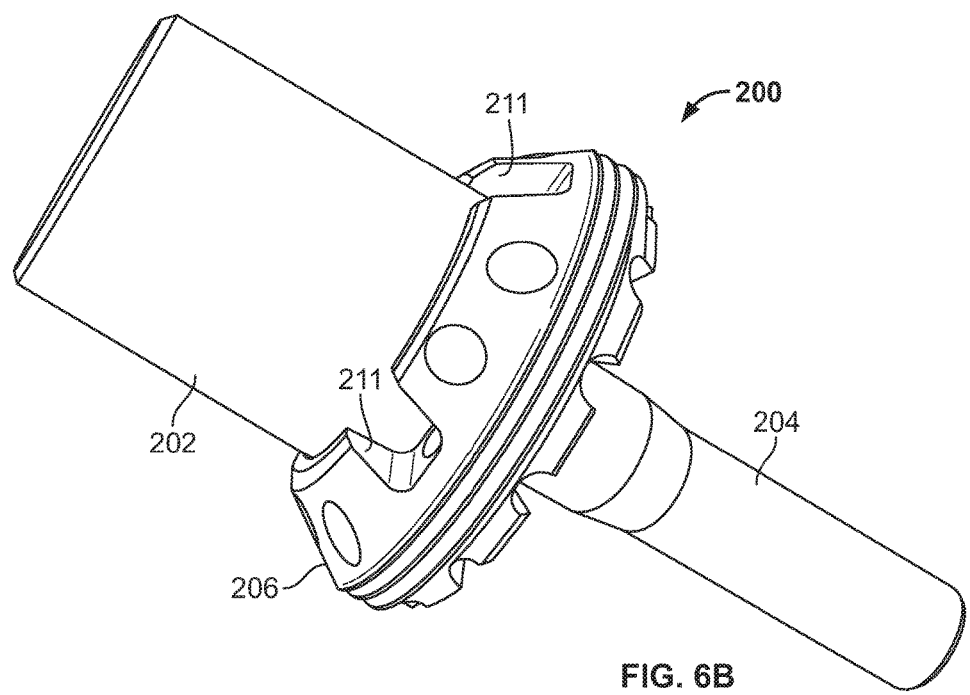
Figure 6C:
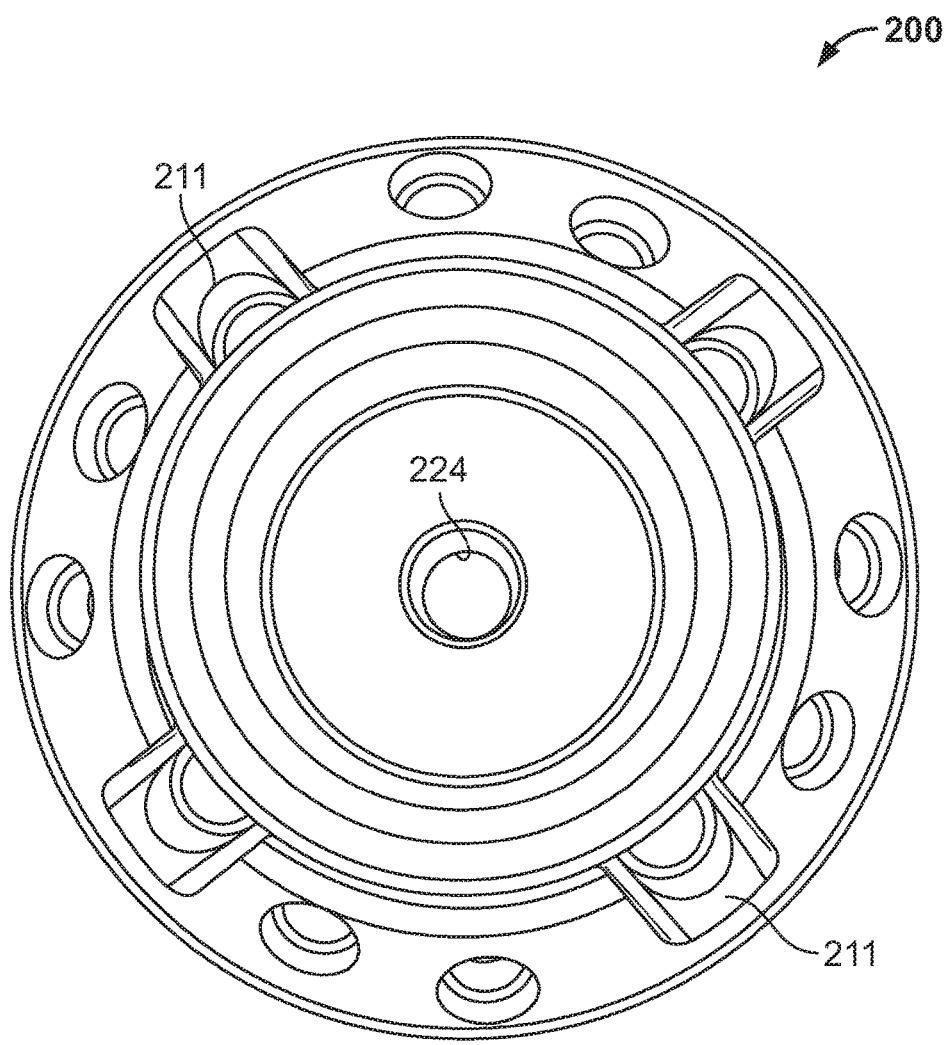
Figure 7B:
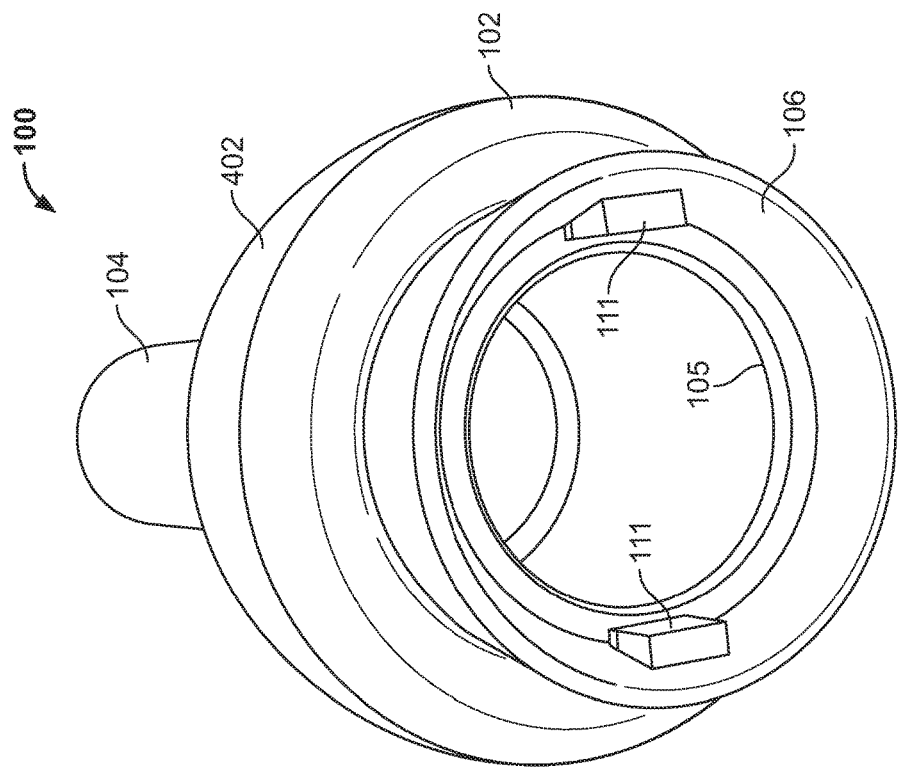
FIGS. 7A and 7B are perspective views of a transdermal adapter for an exemplary transdermal intraosseous device according to the present teachings.
Figure 7A:
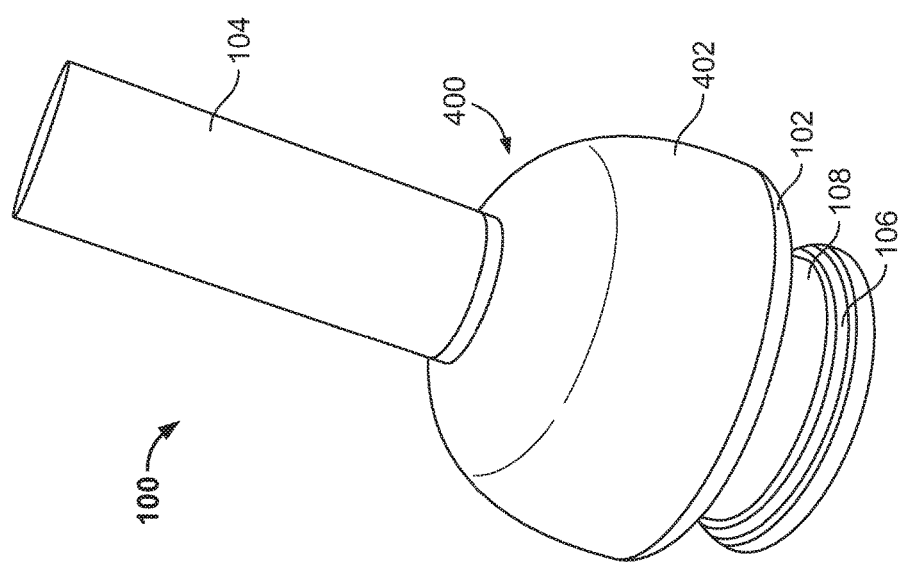

Referring to FIGS. 1A, 1B, 2, 7A and 7B, the transdermal adapter 100 can include a body 101 having a substantially dome-shaped portion 102 received subcutaneously, and an external shaft 104. The body 101, including the dome-shaped portion 102 and the external shaft 104 can be made as a monolithic (single) piece from a biocompatible metal, such as polished titanium alloy (Ti-6-4). The dome-shaped portion 102 includes an internal bore or opening 105. The internal bore 105 can be tapered and receive a tapered distal portion 202 of the bone fixator 200 for a taper connection therebetween. In some embodiments, an extension 106 can depend proximally from the dome-shaped portion 102 toward the bone of the patient defining a circumferential slot or groove 108. A redundant connector 350 can be used to provide an additional secured connection between the intermediate portion 206 of the bone fixator 200 and the extension 106 of the transdermal adapter 100. The redundant connector 350 can engage the groove 108 and can be, for example, a two-piece split locking nut or washer, as illustrated in FIG. 1A. The redundant connector 350 can be tightened against the intermediate portion with a connector element, such as a screw or other fastener (not shown) and can also provide a tapered engagement with a corresponding tapered portion of the outer surface of the intermediate portion 206. Referring to FIGS. 7B and 6B, a plurality of tabs 111 can protrude from the internal bore 105 for engagement with corresponding slots 211 of the intermediate portion 206 of the bone fixator 200.

Figure 2:
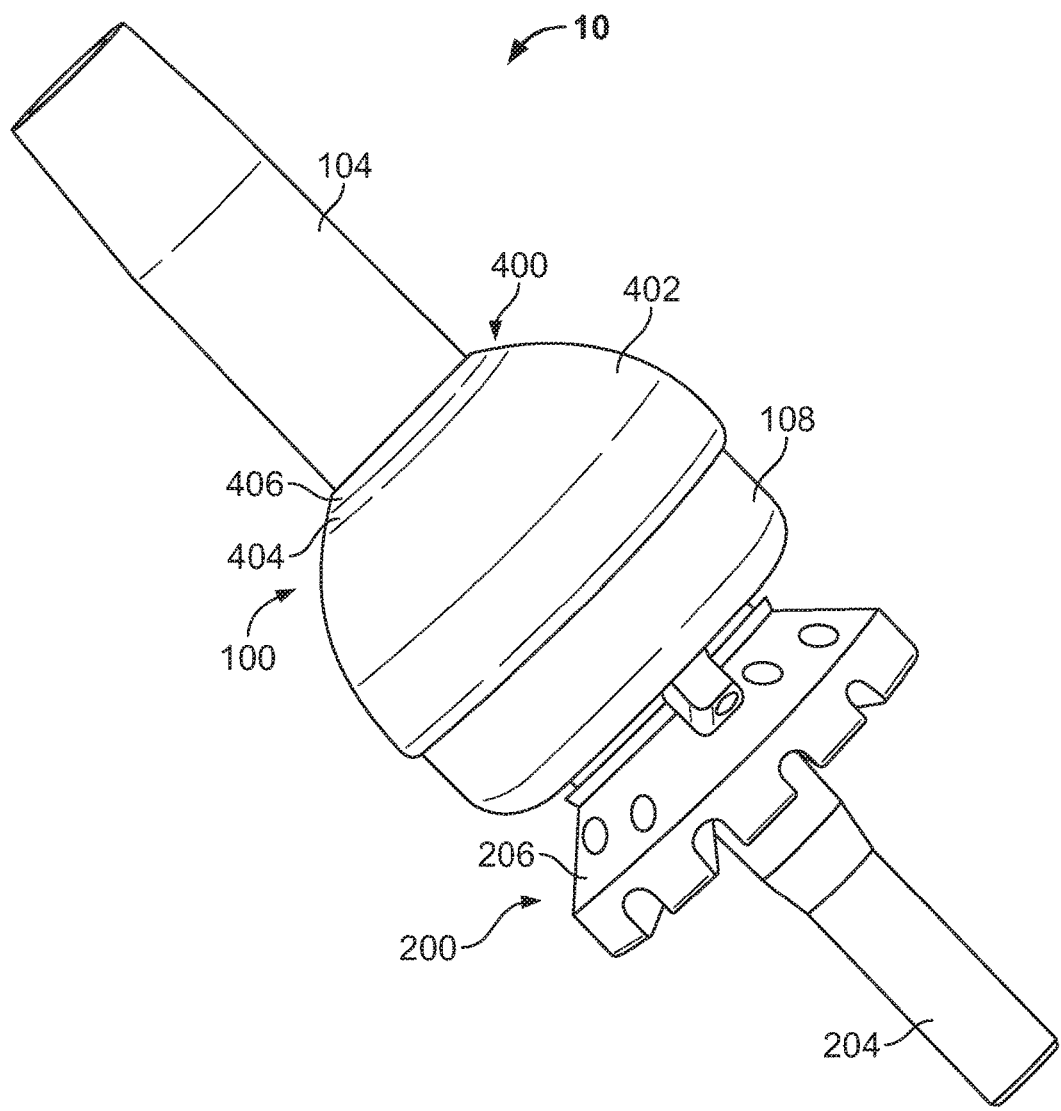
FIG. 2 is an isometric view of an exemplary transdermal intraosseous device according to the present teachings.
Figure 4:
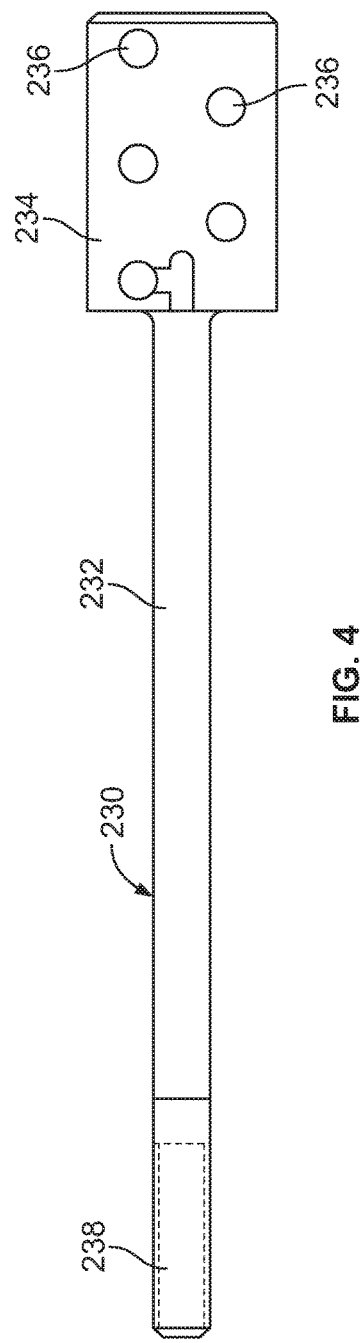
FIG. 4 is an exemplary anchor member of a transdermal intraosseous device according to the present teachings.
Figure 5:
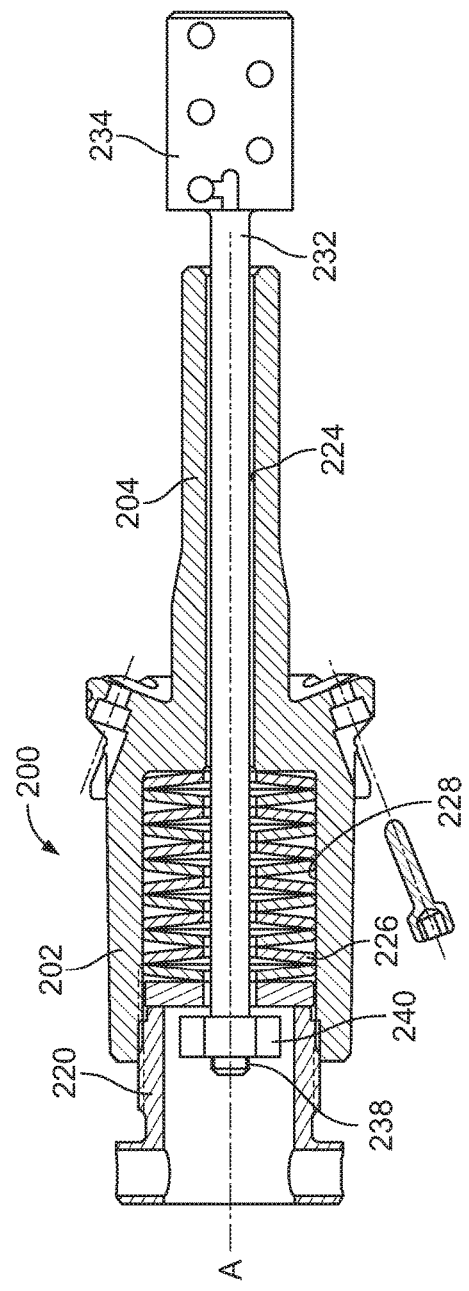
FIG. 5 is a sectional view of the compliant fixator of FIG. 3B shown assembled with the anchor member of FIG. 4.

Regarding infection control, and referring to FIGS. 1A, 1B and 2, the transdermal intraosseous device 10 of the present teachings can include a dermal transition structure 400 between the body 101 of the transdermal adapter 100 and the dermis and epidermis 86 of the patient. The dermal transition structure 400 can include a porous metal dome-shaped structure 402 surrounding and overlaying on the dome-shaped portion 102 of the transdermal adapter 100. The material of the porous metal dome-shaped structure 402 can be, for example, the Regenerex® Porous Titanium Construct discussed above. The porous metal dome-shaped structure 402 can be attached to the dome-shaped structure 402 with laser welding, brazing, sintering, or other methods.

The dermal transition structure 400 can also provide a controlled roughness gradient from the smooth/polished external shaft 104 to the porous metal dome-shaped structure 402. Accordingly, first and second transitional surface treatment layers 404, 406 can be included at the interface between the transdermal adapter 100 and the dermis/epidermis 86 for providing a roughness gradient. A first transitional surface treatment layer 404 is positioned and extends directly above the porous metal dome-shaped structure 402 surrounding a contiguous portion of the external shaft 104 along the longitudinal axis A and contacting the dermis 86. The first transitional surface treatment layer 404 can be a roughness treatment on the external shaft 104 formed by blasting, including ceramic bead blasting, sand blasting, grit blasting and similar treatments.

The second transitional surface treatment layer 406 is contiguous to the first transitional surface treatment layer 404 and includes a blasting treatment in combination with acid etching, such as an Osseotite® treated surface. Osseotite® is a surface treatment commercially available from Biomet, Inc., Warsaw, Ind. Osseotite® treated surfaces may yield up to 110% increase in platelet adhesion and up to 54% increase in red blood cell (RBD) agglomeration over a smooth machined surface. RBD agglomeration is known to enhance blood clot permeability, which promotes wound healing. Increased platelet activity can also lead to enhanced wound healing through the release of cytokines and growth factors such as platelet derived growth factor (PDGF)-AB and transforming growth factor (TGF)-beta1.

The dermal transition structure 400 provides a gradual transition from the polished outer surface of the external shaft 104 to the rough surface of the porous metal dome-shaped structure 402 through the first and second transitional surface treatment layers 404, 406. Thus, the first transitional surface treatment layer 402, has greater roughness than the second transitional surface treatment layer 404.

The dermal transition structure 400 may enhance dermal connective tissue adhesion, given that dermal tissue preferentially adheres to substrates with percentage porosity and pore size similar to porosity of the porous metal dome-shaped structure 402 and the Regenerex® material, as described above. The roughness gradient from the porous metal dome-shaped structure 402 to the polished shaft 104 through the first and second layers 404, 406 described above may provide dermal tissue ingrowth as well epidermal adhesion, as described above.

As discussed above, the bone fixator 200 can be a compliant fixator configured to provide a bone biasing force to a portion of a bone. Any known compliant fixator can be used, including, but not limited to, the compliant fixators disclosed in commonly assigned U.S. Pat. Nos. 7,141,073, 6,712,855, 6,508,841, 6,197,065, all of which are assigned to common assignee Biomet Manufacturing Corp., and are incorporated herein by reference. The compliant fixator 200 is adapted to provide a compressive load on the bone, thereby reducing bone loss and promoting bone growth. The compliance of the bone fixator 200 can exceed that of native bone 80, such that stress shielding does not occur. Additionally, the native bone 80 can experiences physiologic dynamic compressive loading biased by a preset spring compression. In this context, evidence of bone hypertrophy or lack of bone loss may occur near the resection level resulting in increased bone strength, possibly as a result of a phenomenon known as Wolf's Law.

Referring to FIGS. 3A-5, an exemplary compliant bone fixator 200 can include, for example, a compliant member 226. The compliant member 226 can be include one or more compliant elements, such as one or more Belleville washers, as shown in FIG. 3B or other spring washers or a single or double helical spring. Detailed descriptions of the structure and operation of various compliant fixators 200 and biasing mechanisms are provided in the above-referenced patents. According to the present teachings, the compliant member 226 ca be contained within a longitudinal bore 228 of the distal portion 202 of the bone fixator. The longitudinal bore 228 is shaped and configured for accommodating the compliant member 226, such that the longitudinal bore 228 may have a larger diameter for Belleville washers than for a helical spring. The compliant bone fixator 200 can be anchored to the bone 80 and pre-stressed via an anchoring member 230. The anchoring member 230 can include an elongated shaft 232 attached to a plug 234 at a first end and having a threaded distal end 238. The plug 234, which can be enlarged relative to the shaft 232, can include a plurality of apertures 236 for receiving transverse bone fixation pins. The anchoring member 230 can be inserted through a longitudinal bore 224 that passes through the bone fixator 200 and through the Belleville washers when used as a compliant member 226. The compliant member 226 can be held temporarily secured using a removable tubular knob 220 having a bore 222. In this regard, the compliant bone fixator 200 can be inserted through a hole/incision punched through the skin and anchored into the bone 80 via the anchoring member 230 while the compliant member 226 is held with the tubular knob 220. A nut 240 can be threaded on to the distal threaded portion 238 of the shaft 232 and rotated to pre-stress the compliant member 226 to a desired amount. The knob 220 may then be removed. The transdermal adapter 100 can be impacted in position for locking the tapered connection between the dome-shaped portion 102 of the transdermal adapter 100 and the distal portion 202 of the bone fixator 200. The transdermal adapter can also be locked with the redundant connector 350. The skin flap around the incision can be sutured around the external shaft 104.

Figure 9:
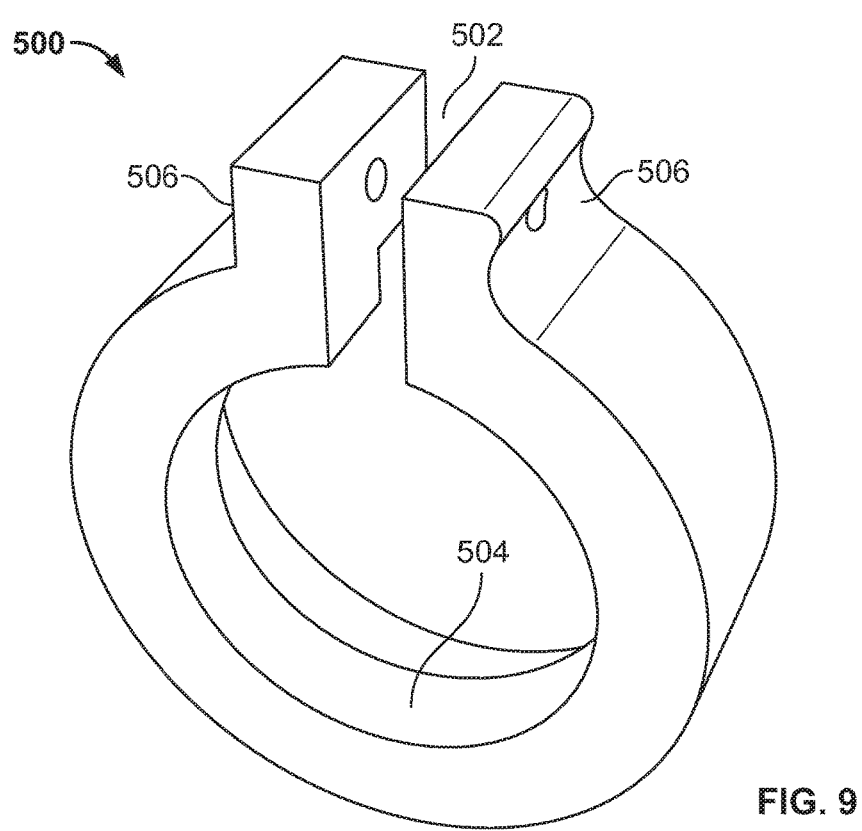
FIG. 9 is a perspective view of an exemplary quick release collar of a transdermal intraosseous device according to the present teachings.
Figure 10:
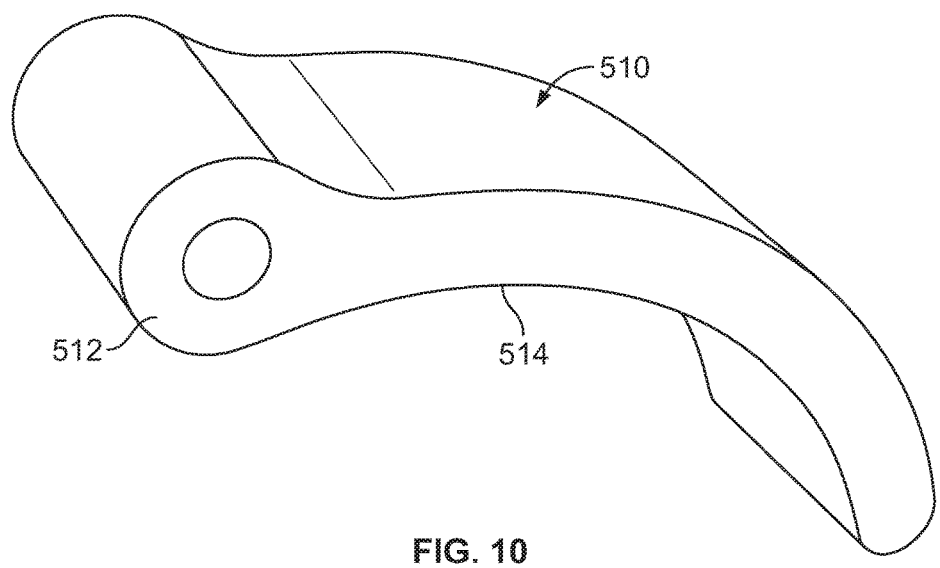
FIG. 10 is a perspective view of an exemplary quick release lever of a transdermal intraosseous device according to the present teachings.
Figure 12:
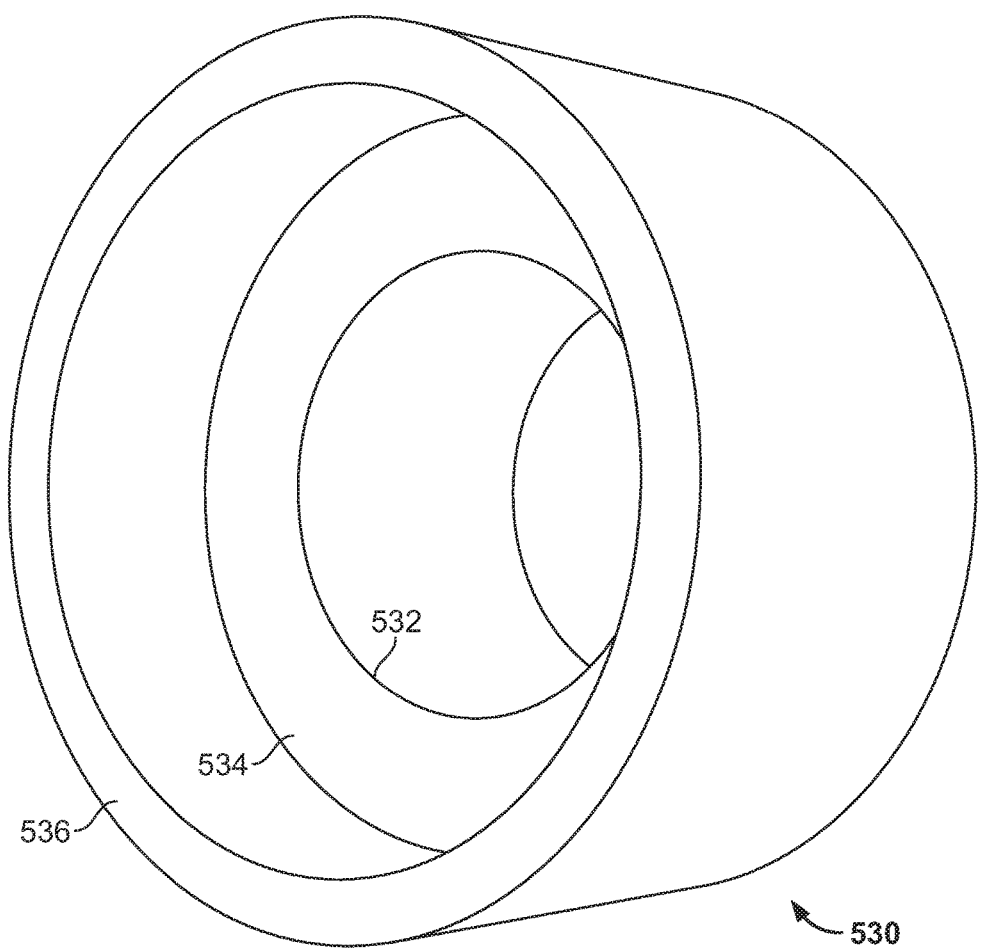
FIG. 12 is an exemplary torque limiter of a transdermal intraosseous device according to the present teachings.

The compliant bone fixator 200 can be designed to have a fatigue strength which is substantially greater than expected and/or estimated loads transmitted from an external prosthetic device to the bone-implant interface. Referring to FIGS. 1A and 12, as an added precaution, a torque limiter 530 can be installed in series with the exoprosthetic device 10 to prevent a large torsional load transmission to the compliant bone fixator 200 in the case of trauma or other unexpectedly high load. The torque limiter 530 can be, for example, a two piece stepped device including first and second tubular shafts 534, 536 with a common through bore 532 receiving a portion of the external shaft 104 of the body 101 of the transdermal adapter 100. The torque limiter 530 can be, for example, a torque limiter commercially available from R+W America, Bensenville, Ill. The torque limiter 530 can be coupled to the external shaft 104 with a quick release collar 500. An exemplary collar 500 is illustrated in FIG. 9 and includes a central aperture 504 and two end portions 506 defining a gap (slit in the collar). The collar 500 can be locked and unlocked with an actuating mechanism, such as a cammed lever 510. An exemplary cammed lever is illustrated in FIG. 10 and includes a coupling end 512 and a curved engagement surface 514.

Figure 11:
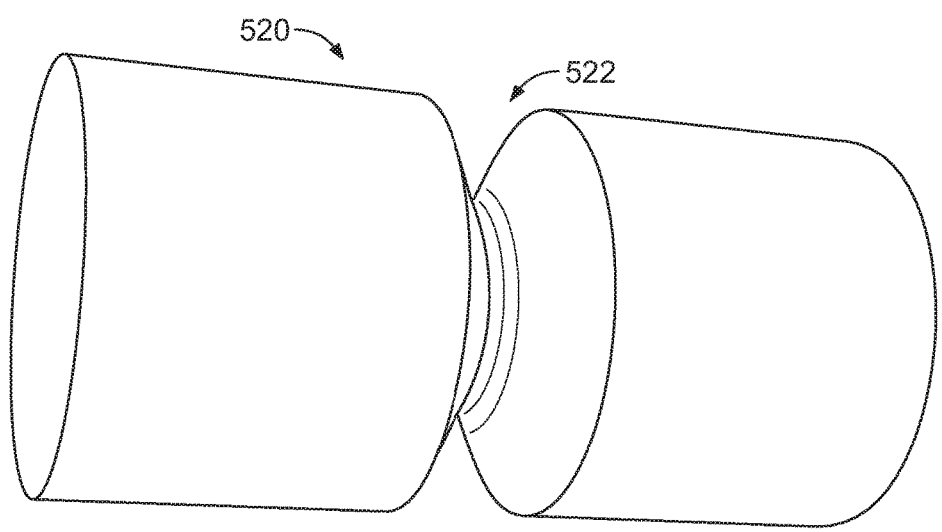
FIG. 11 is an exemplary output shaft of a transdermal intraosseous device according to the present teachings.

Referring to FIGS. 1A and 11, an exemplary output shaft 520 for the prosthetic device is illustrated. The output shaft 520 can include a notch 522 to control a failure mode and location in bending.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings.

What is claimed is:

1. A transdermal intraosseous device comprising:
   a transdermal adapter having a longitudinal axis and configured for connection to an external prosthetic device for use with a bone of a patient, the transdermal adapter including:
   a dome-shaped portion for transcutaneous implantation,
   a porous metal dome-shaped structure at least partially overlaying the dome-shaped portion,
   an external shaft extending from the dome-shaped portion, the external shaft including a polished external shaft portion, and
   a dermal transition structure extending axially from the porous metal dome-shaped structure to the polished external shaft portion, the dermal transition structure including a first transitional surface treatment layer contiguous to a second transitional surface treatment layer such that a common border of the first and second transitional surface treatment layers is located along the longitudinal axis and each of the first and second transitional surface treatment layers extends along the external shaft distal of the dome-shaped portion, each of the first and second transitional surface treatment layers configured to directly contact a dermis layer of the patient for infection control upon implantation thereof, the first transitional surface treatment layer having a greater roughness than the second transitional surface treatment layer to provide a controlled roughness gradient from the external shaft to the dome-shaped portion for controlling infection at the dermis layer of the patient, wherein a first surface treatment of the first transitional surface treatment layer is different than a second surface treatment of the second transitional surface treatment layer; and
   a bone fixator including a distal portion coupled to the transdermal adapter and a proximal portion configured for anchoring into the bone.

2. The transdermal intraosseous device of claim 1, wherein the external shaft and the dome-shaped portion of the transdermal adapter are monolithically coupled.

3. The transdermal intraosseous device of claim 1, wherein the polished external shaft portion extends directly distal of the dermal transition structure along the longitudinal axis.

4. The transdermal intraosseous device of claim 3, wherein the first transitional surface treatment layer is a roughness treatment of the external shaft.

5. The transdermal intraosseous device of claim 4, wherein the roughness treatment of the first transitional surface treatment layer is selected from the group consisting of ceramic bead blasting, sand blasting and grit blasting.

6. The transdermal intraosseous device of claim 4, wherein the second transitional surface treatment layer comprises a combination of blasting treatment and acid etching to configure the second transitional surface treatment layer for contact with the dermis layer of the patient.

7. The transdermal intraosseous device of claim 6, wherein the dome-shaped portion includes an internal bore receiving the distal portion of the bone fixator with a taper connection therebetween.

8. The transdermal intraosseous device of claim 7, wherein the bone fixator includes a compliant biasing member within a bore in the distal portion of the bone fixator, wherein the compliant biasing member is pre-stressed and configured to provide a compressive force to the bone.

9. The transdermal intraosseous device of claim 8, further comprising a centering sleeve having an outer surface configured to be engageable with a bore in the bone and an inner surface receiving the proximal portion of the bone fixator.

10. The transdermal intraosseous device of claim 1, wherein the porous metal dome-shaped structure has an average porosity of 67 percent.

11. The transdermal intraosseous device of claim 1, wherein the porous metal dome-shaped structure has a pore size ranging from 100 to 600 microns.

12. The transdermal intraosseous device of claim 1, wherein the porous metal dome-shaped structure has an average pore size of 300 microns.

13. A transdermal intraosseous device comprising:
   a transdermal adapter including a longitudinal axis and configured for connection to an external prosthetic device for use with a bone of a patient, the transdermal adapter including:
   a dome-shaped portion for transcutaneous implantation;
   a porous metal dome-shaped structure at least partially surrounding and overlaying the dome-shaped portion of the transdermal adapter; and
   an external shaft extending from the dome-shaped portion, the external shaft including:
   a first transitional surface treatment layer adjacent the porous metal dome-shaped structure, the first transitional surface treatment layer contiguous to a second transitional surface treatment layer, each of the first and second transitional surface treatment layers extending along the external shaft distal of the dome-shaped portion; and
   a polished external shaft portion contiguous to the second transitional surface treatment layer; and
   a bone fixator including a distal portion coupled to the transdermal adapter and a proximal portion configured for anchoring into the bone;
   wherein the porous metal dome-shaped structure has a greater roughness than the first transitional surface treatment layer, the first transitional surface treatment layer has a greater roughness than the second transitional surface treatment layer, and the second transitional surface treatment layer having a greater roughness than the polished external shaft portion, and wherein the first and second transitional surface treatment layers and the porous metal dome-shaped structure are configured to create a roughness gradient from the porous metal dome-shaped structure to the polished external shaft portion with each layer of the roughness gradient being configured to directly contact a dermis layer of the patient for infection control upon implantation thereof.

* * * * *